US008043864B2

(12) United States Patent
Stroup

(10) Patent No.: US 8,043,864 B2
(45) Date of Patent: Oct. 25, 2011

(54) FINGER SWIPE FLUID-TRANSFER COLLECTION ASSEMBLY AND METHOD OF USING THE SAME

(75) Inventor: David Karl Stroup, El Cajon, CA (US)

(73) Assignee: Infusion Innovations, Inc., La Jolla, CA (US)

( * ) Notice: Subject to any disclaimer, the term of this patent is extended or adjusted under 35 U.S.C. 154(b) by 148 days.

(21) Appl. No.: 12/547,314

(22) Filed: Aug. 25, 2009

(65) Prior Publication Data

US 2010/0050789 A1 Mar. 4, 2010

Related U.S. Application Data

(60) Provisional application No. 61/091,784, filed on Aug. 26, 2008.

(51) Int. Cl.
*G01N 1/14* (2006.01)

(52) U.S. Cl. ......................... 436/180; 436/164; 422/505

(58) Field of Classification Search ........................ None
See application file for complete search history.

(56) References Cited

U.S. PATENT DOCUMENTS

| | | | |
|---|---|---|---|
| 3,640,388 A | 2/1972 | Ferrari | |
| 4,014,328 A | 3/1977 | Cluff et al. | |
| 4,685,472 A | 8/1987 | Muto | |
| 5,029,583 A | 7/1991 | Meserol et al. | |
| 5,096,669 A | 3/1992 | Lauks et al. | |
| 5,505,212 A | 4/1996 | Keljmann et al. | |
| 5,595,187 A | 1/1997 | Davis | |
| 5,636,640 A | 6/1997 | Staehlin | |
| 5,800,779 A | 9/1998 | Johnson | |
| 6,258,045 B1 | 7/2001 | Ray et al. | |
| 6,426,213 B1 | 7/2002 | Eisenson | |
| 6,660,527 B2 | 12/2003 | Stroup | |
| 2001/0007926 A1 | 7/2001 | Trudil | |
| 2001/0008614 A1 | 7/2001 | Aronowitz | |
| 2004/0121481 A1* | 6/2004 | Stroup | 436/165 |
| 2006/0216212 A1* | 9/2006 | Lum et al. | 422/103 |

FOREIGN PATENT DOCUMENTS

| | | |
|---|---|---|
| JP | 11-183468 A | 7/1999 |
| JP | 11-183469 A | 7/1999 |
| KR | 10-2008-0040690 A | 5/2008 |
| WO | 98-44331 A1 | 10/1998 |

OTHER PUBLICATIONS

International Search Report and Written Opinion issued in PCT/US2009/054931 on Apr. 8, 2010, 10 pages.

* cited by examiner

*Primary Examiner* — Yelena G Gakh
*Assistant Examiner* — Christopher A Hixson
(74) *Attorney, Agent, or Firm* — Stephen C. Beuerle; Procopio Cory Hargreaves & Savitch LLP

(57) ABSTRACT

A method of using a finger swipe fluid transfer collection assembly includes providing a finger swipe fluid transfer collection assembly including a base, a test media carried by the base, an inlet for receiving a sample fluid, an outlet, a finger swipe fluid transfer mechanism carried by the base between the inlet and the outlet and including an interior; swiping the finger swipe fluid transfer mechanism with one's finger to impart a negative pressure in the interior of the finger swipe fluid transfer mechanism to draw the sample fluid into the interior of the finger swipe fluid transfer mechanism through the inlet; and swiping the finger swipe fluid transfer mechanism again with one's finger to impart a positive pressure in the interior of the finger swipe fluid transfer mechanism to pump the sample fluid through the outlet and be transferred to the test media.

19 Claims, 1 Drawing Sheet

FINGER SWIPE FLUID-TRANSFER COLLECTION ASSEMBLY AND METHOD OF USING THE SAME

CROSS-REFERENCE TO RELATED APPLICATION

This application claims the benefit of provisional patent application 61/091,784, filed Aug. 26, 2008 under 35 U.S.C. 119(e). This provisional patent application is incorporated by reference herein as though set forth in full.

FIELD OF THE INVENTION

The present invention is, in general, in the fields of fluid-transfer collection assemblies and fluid-transfer pumping assemblies.

BACKGROUND OF THE INVENTION

Collection kits used for testing one or more analytes of a sample include multiple separate components such as a pipettes, collection tubes, vials or ampoules containing needed diluents or reagents, and test media devices. Because these collection kits have so many separate pieces, in most cases, use of such collection kits has been limited to a laboratory. Simple tests may be performed outside of the laboratory using only test media devices, but these test media devices are limited as to the types of tests that can be performed. More elaborate tests require diluents, pipettes, collection tubes, etc., and are difficult and awkward to perform outside of the laboratory.

Accordingly, a need exists for a simple fluid transfer and mixing collection assembly that does not include numerous separate pieces, is easy to use, can be used for multiple different types of tests and can be used in and outside a laboratory.

SUMMARY OF THE INVENTION

Accordingly, an aspect of the invention involves a finger swipe fluid transfer and mixing collection assembly. The collection assembly includes a foil base, a flexible polyethylene top surface, a test media carried by the base, an inlet for receiving a sample fluid, an outlet, and a finger-swipe fluid transfer mechanism carried by the base between the inlet and the outlet and including an interior, which may include a second fluid therein. The finger swipe fluid transfer mechanism, when swiped with a user's finger, acts as a pump to draw sample fluid through the inlet and into an interior of the finger swipe fluid transfer mechanism. A second fluid may be disposed in the interior so that drawing the sample fluid into the interior of the finger swipe fluid transfer mechanism causes the sample fluid to mix with the second fluid. Alternatively, the sample fluid may be the only fluid transferred through the collection assembly. To transfer the mixed sample fluid and second fluid (or only the sample fluid) from the interior of the finger swipe fluid transfer mechanism to the test media for testing, the user swipes the finger swipe fluid transfer mechanism again with one's finger.

Another aspect of the invention involves a method of using a finger swipe fluid transfer collection assembly. The method includes providing a finger swipe fluid transfer collection assembly including a base, a test media carried by the base, an inlet for receiving a sample fluid, an outlet, a finger swipe fluid transfer mechanism carried by the base between the inlet and the outlet and including an interior; swiping the finger swipe fluid transfer mechanism with one's finger to impart a negative pressure in the interior of the finger swipe fluid transfer mechanism to draw the sample fluid into the interior of the finger swipe fluid transfer mechanism through the inlet; and swiping the finger swipe fluid transfer mechanism again with one's finger to impart a positive pressure in the interior of the finger swipe fluid transfer mechanism to pump the sample fluid through the outlet and be transferred to the test media.

A further aspect of the invention involves a finger swipe fluid transfer collection assembly includes a base; a test media carried by the base; an inlet for receiving a sample fluid; an outlet; and a finger swipe fluid transfer mechanism carried by the base between the inlet and the outlet and including an interior, the finger swipe fluid transfer mechanism swipeable with one's finger to impart a negative pressure in the interior of the finger swipe fluid transfer mechanism to draw the sample fluid into the interior of the finger swipe fluid transfer mechanism through the inlet, and swipeable again with one's finger to impart a positive pressure in the interior of the finger swipe fluid transfer mechanism to pump the sample fluid through the outlet and be transferred to the test media.

Other and further objects, features, aspects, and advantages of the present invention will become better understood with the following detailed description of the accompanying drawings.

DESCRIPTION OF THE PREFERRED EMBODIMENT

Figure 1:
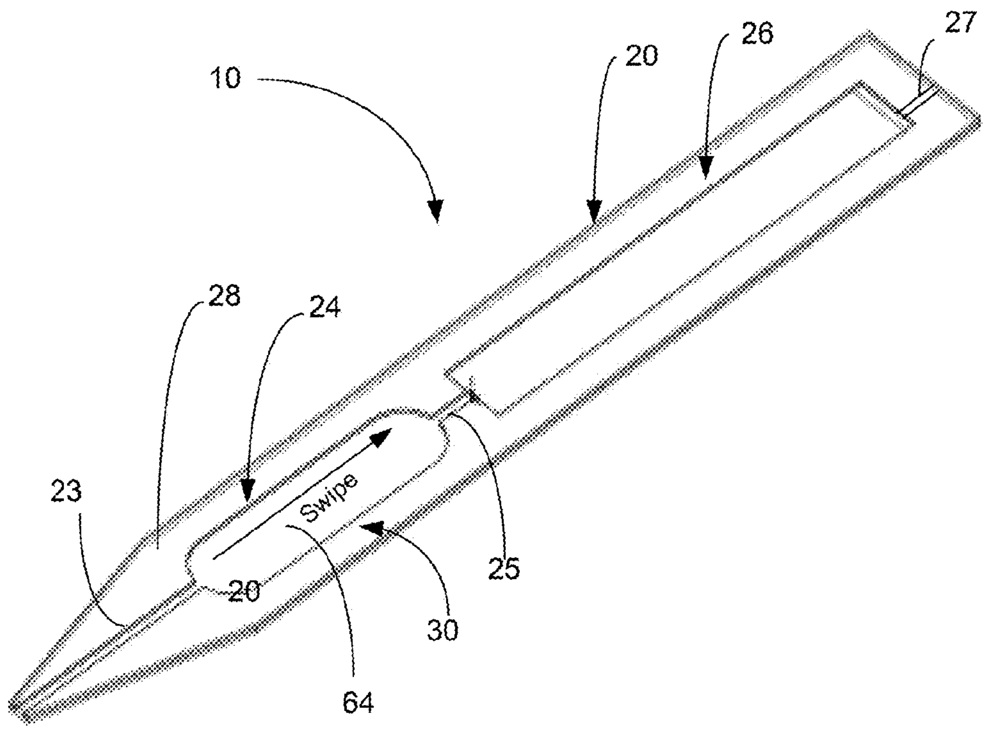
FIG. 1 is a perspective view of a finger-swipe fluid transfer and mixing collection assembly constructed in accordance with an embodiment of the invention.
Figure 2:
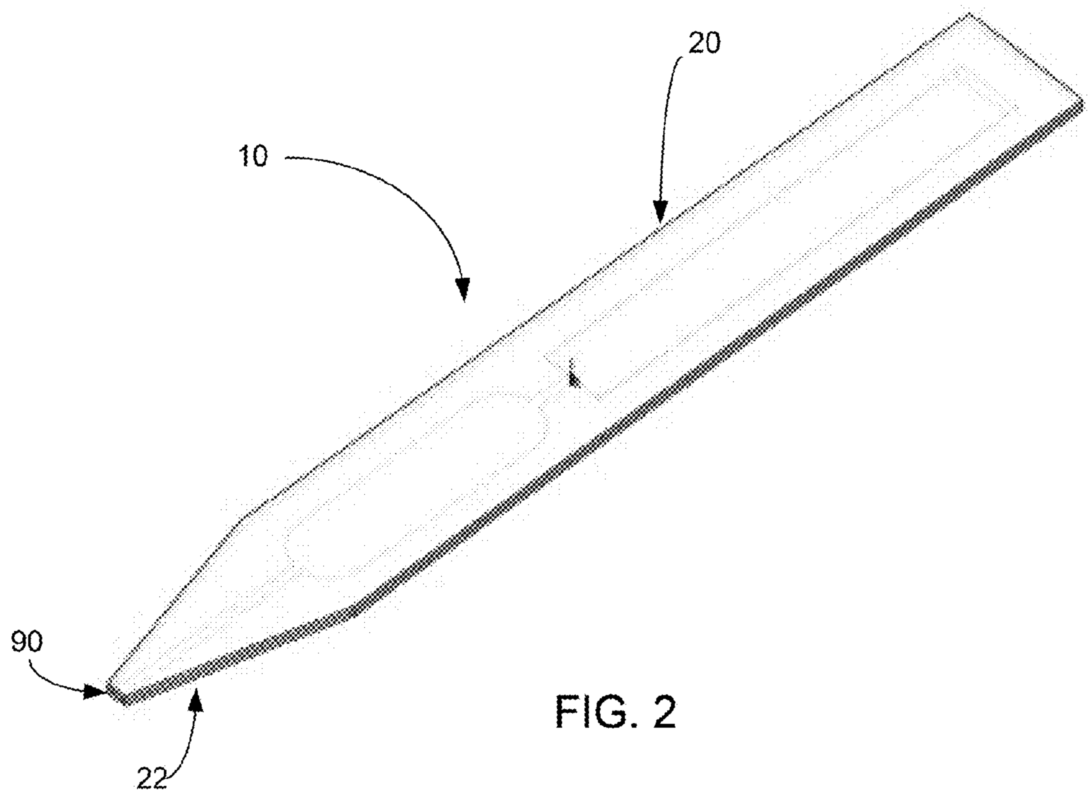
FIG. 2 is a bottom perspective view of the finger-swipe fluid transfer and mixing collection assembly.

With reference to FIGS. 1 and 2, an embodiment of a finger-swipe fluid transfer and mixing collection assembly ("collection assembly") 10, and method of using the same will now be described. Further below, the collection assembly 10 will be described as an optical assay test device in an optical assay test method; however, the collection assembly 10 may be used in other devices, processes, and applications where mixing of two or more fluids and/or delivery of one or more fluids to a collection area is desired. Further, although the finger-swipe fluid transfer and mixing collection assembly 10 will be described as being actuated/swiped with one's thumb from the hand one holds the collection assembly 10, in alternative embodiments, other swiping fingers/digits/structures may be used.

The collection assembly 10 includes a flat, rectangular, elongated, plastic base 20 with a pointed, triangular end 22. The base 20 is made of a foil material. The base 20 includes a checkvalve-less elongated inlet fluid path 23, an elongated rectangular reservoir 24, a checkvalve-less outlet fluid path 25, a test media section 26, and a vent 27. A clear flexible polyethylene top 28 covers an upper surface (and the elongated inlet fluid path 23, the elongated rectangular reservoir 24, the outlet fluid path 25, the test media section 26, and the vent 27) of the base 20. The flexible top 28 over the elongated rectangular reservoir 24 forms a finger swipe fluid transfer mechanism 30.

Although the finger swipe fluid transfer mechanism 30 is shown on a top of the base 20, in alternative embodiments, the finger swipe fluid transfer mechanism 30 is disposed on a bottom of the base 20, a side of the base, or on multiple surfaces of the base 20.

In the embodiment shown, before use, fluid in an interior 64 of finger swipe fluid transfer mechanism 30 is air or is a vacuum; however, in an alternative embodiment, a second fluid (e.g., one or more chemical reagents or diluents) are disposed in the interior 64 of finger swipe fluid transfer mechanism 30. The elongated inlet fluid path 23, the elongated rectangular reservoir 24/interior 64, the outlet fluid path 25, and the test media section 26 form a fluid path 69 for the sample fluid (or sample fluid and second fluid).

The pointed, triangular end 22 includes an inlet port 90, which may receive a sample tube (not shown) for transferring sample fluid there through. The inlet port 90 may be covered with a snap-off cover/tip (not shown). Similarly, the vent 27 may be covered with a snap-off vent cover/tip (not shown) to allow air to escape during the pumping/fluid transferring with collection assembly 10.

In the embodiment shown, the test media section 26 includes one or more test media, which may include visual indicia to visually indicate the presence, absence, or concentration of a target analyte or other target object(s). The test media may include one or more of the following: base strip(s), sample pad(s), conjugate pad(s), membrane(s), and absorbent pad(s).

The collection assembly 10 will now be described in use as an optical assay test device in an exemplary optical assay method of use. The collection assembly 10 and method of use may be used in applications such as, but not by way of limitation, drug screening, chemical analysis, crime/accident scene investigations, ground water testing (EPA), and livestock testing. In alternative embodiments, the collection assembly 10 is used in other fluid transfer and/or fluid collection applications.

The inlet port 90 (or a sample tube 100 in communication with the inlet port 90) may be put in communication with a fluid sample source for obtaining a fluid sample. The fluid sample may be any fluid medium such as, but not by way of limitation, a gas, a liquid, a suspension, an extracted or dissolved sample, or a supercritical fluid, as long as some flow properties exist in the sample. The sample may include one or more target analytes of interest for detection. Example analytes include, but not by way of limitation, antigens, antibodies, receptors, ligands, chelates, proteins, enzymes, nucleic acids, DNA, RNA, pesticides, herbicides, inorganic or organic compounds or any material for which a specific binding reagent may be found.

The flexible top 28 over the elongated rectangular reservoir 24 forming the finger swipe fluid transfer mechanism 30 is actuated/swiped with one's thumb from the same hand one uses to hold the collection assembly 10, in the direction of the swipe arrow shown. The swiping of the finger swipe fluid transfer mechanism 30 causes a vacuum force to be created in the elongated rectangular reservoir 24, drawing the sample fluid through the checkvalve-less elongated inlet fluid path 23 and into the elongated rectangular reservoir 24. In the embodiment of the collection assembly 10 where a second fluid is disposed in the elongated rectangular reservoir 24, the sample fluid drawn into the elongated rectangular reservoir 24 is mixed with the second fluid (e.g., the sample fluid mixes and reacts with reagent). The finger swipe fluid transfer mechanism 30 is actuated/swiped again with one's thumb. This forces the sample fluid in the elongated rectangular reservoir 24 (or the mixed sample fluid and second fluid) to be transferred through the checkvalve-less outlet fluid path 25, and to one or more test media in the test media section 26. Visual indicia of the one or more test media may indicate the presence, absence, or concentration of a target analyte for the optical assay method. Air built up in the collection assembly 10 escapes from the collection assembly 10 through the vent 27. Because the flexible polyethylene top 28 is clear, fluid transfer through the collection assembly 10 can be seen by the user.

Numerous features, implementations, and embodiments of the collection assembly 10 will now be described. The collection assembly 10 may be used more than once to perform the same test, different tests, or may be disposed of after single use. Different collection assemblies 10 may be used to perform different tests. The collection assembly 10 may be used to test for the presence, absence, or concentration of one or more analytes. The collection assembly 10 may be held and operated with a single hand of a user. The user may operate the finger swipe fluid transfer mechanism 30 with a thumb of the same hand used to hold the collection assembly 10. In an alternative embodiment, the collection assembly 10 may have more than one finger swipe fluid transfer mechanism 30. The collection assembly 10 is especially advantageous in that the multiple transfer and/or mixing steps can all be done with a single hand of the user with a simple thumb swiping motion from the same hand as that used to hold the collection assembly 10.

The collection assembly 10 is advantageous because it has fewer parts that other pump designs; no pump components nor check valves are required. Because the collection assembly 10 is so simple to use, the collection assembly 10 may be used by the user for testing in the field, in the lab, and in the home for a wide variety of applications.

The above description of the disclosed embodiments is provided to enable any person skilled in the art to make or use the invention. Various modifications to these embodiments will be readily apparent to those skilled in the art, and the generic principles described herein can be applied to other embodiments without departing from the spirit or scope of the invention. Thus, it is to be understood that the description and drawings presented herein represent a presently preferred embodiment of the invention and are therefore representative of the subject matter which is broadly contemplated by the present invention.

The above figures may depict exemplary configurations for the invention, which is done to aid in understanding the features and functionality that can be included in the invention. The invention is not restricted to the illustrated architectures or configurations, but can be implemented using a variety of alternative architectures and configurations. Additionally, although the invention is described above in terms of various exemplary embodiments and implementations, it should be understood that the various features and functionality described in one or more of the individual embodiments with which they are described, but instead can be applied, alone or in some combination, to one or more of the other embodiments of the invention, whether or not such embodiments are described and whether or not such features are presented as being a part of a described embodiment. Thus the breadth and scope of the present invention, especially in the following claims, should not be limited by any of the above-described exemplary embodiments.

Terms and phrases used in this document, and variations thereof, unless otherwise expressly stated, should be construed as open ended as opposed to limiting. As examples of the foregoing: the term "including" should be read as mean "including, without limitation" or the like; the term "example" is used to provide exemplary instances of the item in discussion, not an exhaustive or limiting list thereof; and adjectives such as “conventional,” “traditional,” “standard,” “known” and terms of similar meaning should not be construed as limiting the item described to a given time period or to an item available as of a given time, but instead should be read to encompass conventional, traditional, normal, or standard technologies that may be available or known now or at any time in the future. Likewise, a group of items linked with the conjunction “and” should not be read as requiring that each and every one of those items be present in the grouping, but rather should be read as “and/or” unless expressly stated otherwise. Similarly, a group of items linked with the conjunction “or” should not be read as requiring mutual exclusivity among that group, but rather should also be read as “and/or” unless expressly stated otherwise. Furthermore, although item, elements or components of the disclosure may be described or claimed in the singular, the plural is contemplated to be within the scope thereof unless limitation to the singular is explicitly stated. The presence of broadening words and phrases such as “one or more,” “at least,” “but not limited to” or other like phrases in some instances shall not be read to mean that the narrower case is intended or required in instances where such broadening phrases may be absent.

I claim:

1. A method of using a finger swipe fluid transfer collection assembly, comprising:

providing a finger swipe fluid transfer collection assembly including a base, a test media carried by the base, an inlet for receiving a sample fluid, an outlet, a finger swipe fluid transfer mechanism carried by the base between the inlet and the outlet and including an interior in open communication with the inlet, the outlet, and the test media and without valves there between;

swiping the finger swipe fluid transfer mechanism with one’s finger to impart a negative pressure in the interior of the finger swipe fluid transfer mechanism to draw the sample fluid into the interior of the finger swipe fluid transfer mechanism through the inlet;

swiping the finger swipe fluid transfer mechanism again with one’s finger to impart a positive pressure in the interior of the finger swipe fluid transfer mechanism to pump the sample fluid through the outlet and be transferred to the test media.

2. The method of claim 1, wherein the interior of the finger swipe fluid transfer mechanism includes a second fluid, and swiping the finger swipe fluid transfer mechanism with one’s finger imparts a negative pressure in the interior of the finger swipe fluid transfer mechanism to draw the sample fluid into the interior of the finger swipe fluid transfer mechanism through the inlet to mix with the second fluid; and swiping the finger swipe fluid transfer mechanism again with one’s finger impart a positive pressure in the interior of the finger swipe fluid transfer mechanism to pump the mixed sample fluid and second fluid through the outlet and be transferred to the test media.

3. The method of claim 1, wherein the finger swipe fluid transfer mechanism is longitudinally elongated and swiping includes applying pressure to the finger swipe fluid transfer mechanism with one’s finger while moving one’s finger in an inlet-to-outlet longitudinal direction along the finger swipe fluid transfer mechanism.

4. The method of claim 1, wherein the base is a flat, rectangular, elongated base.

5. The method of claim 1, wherein the inlet and the outlet are checkvalve-less.

6. The method of claim 1, wherein the base includes a vent.

7. The method of claim 1, wherein the base includes a tip.

8. The method of claim 1, wherein the base includes an outer surface and a clear flexible polyethylene top covers the outer surface of the base.

9. The method of claim 8, wherein a portion of the clear flexible polyethylene top forms the finger swipe fluid transfer mechanism.

10. The method of claim 1, wherein the finger swipe fluid transfer collection assembly further includes a sample tube having a proximal end connected to the inlet and a distal end, and the method further includes communicating the distal end of the sample tube with the sample fluid to draw the sample fluid into the interior of the finger swipe fluid transfer mechanism.

11. The method of claim 10, wherein the sample tube is at least one of fixed to the inlet, retractable, not retractable, locked to the inlet, not locked to the inlet, detachably connectable to the inlet.

12. The method of claim 1, wherein the finger swipe fluid transfer collection assembly further includes at least one of a wick, sponge, open-cell foam, porous material, and an absorbent material connected to the inlet, and the method further includes communicating at least one of the wick, sponge, open-cell foam, porous material, and an absorbent material with the sample fluid to draw the sample fluid into the interior of the finger swipe fluid transfer mechanism.

13. The method of claim 1, wherein the method is an assay test method, the sample fluid includes an analyte of interest for assay testing, the second fluid is a reagent, and the test media visually indicates the presence or absence of an analyte of interest.

14. The method of claim 1, wherein the method is a test method for testing at least one of drug screening, chemical analysis, crime/accident scene investigations, ground water testing (EPA), and livestock testing.

15. The method of claim 1, wherein the sample fluid is a fluid medium of at least one of a gas, a liquid, a suspension, an extracted or dissolved sample, and a supercritical fluid.

16. The method of claim 1, wherein the sample fluid includes a sample including one or more target analytes of interest for detection.

17. The method of claim 16, wherein the one or more target analytes of interest include at least one of antigen, antibody, receptor, ligands chelate, protein, enzyme, nucleic acid, DNA, RNA, pesticide, herbicide, inorganic compound, organic compounds, a material for which a specific binding reagent exists.

18. The method of claim 1, wherein test media indicates at least one of presence, absence, and concentration of one or more analytes.

19. The method of claim 1, wherein the finger swipe fluid transfer collection assembly includes multiple finger swipe fluid transfer mechanisms.

* * * * *